United States Patent [19]

Ashe et al.

[11] Patent Number: 5,699,269

[45] Date of Patent: Dec. 16, 1997

[54] METHOD FOR PREDICTING CHEMICAL OR PHYSICAL PROPERTIES OF CRUDE OILS

[75] Inventors: Terrence Rodney Ashe, Point Edward; Stilianos George Roussis, Brights Grove; James Wade Fedora, Sarnia; Gerald Felsky, Sarnia; William Patrick Fitzgerald, Sarnia, all of Canada

[73] Assignee: Exxon Research and Engineering Company, Florham Park, N.J.

[21] Appl. No.: 494,203

[22] Filed: Jun. 23, 1995

[51] Int. Cl.$^6$ ........................................... G01J 3/42
[52] U.S. Cl. ........................ 364/499; 436/29; 436/60
[58] Field of Search ........................... 364/496, 497, 364/498, 499, 500; 395/911, 928; 436/29, 60

[56] References Cited

U.S. PATENT DOCUMENTS

| | | | |
|---|---|---|---|
| 4,800,279 | 1/1989 | Hieftje et al. | 250/339.12 |
| 5,119,315 | 6/1992 | Kemp et al. | 364/498 |
| 5,121,337 | 6/1992 | Brown | 364/498 |
| 5,218,529 | 6/1993 | Meyer et al. | 364/413.01 |
| 5,360,972 | 11/1994 | DiFoggio et al. | 364/498 |
| 5,412,581 | 5/1995 | Tackett | 364/497 |
| 5,424,959 | 6/1995 | Reyes et al. | 364/498 |
| 5,446,681 | 8/1995 | Gethner et al. | 364/498 |
| 5,452,232 | 9/1995 | Espinosa et al. | 364/498 |

FOREIGN PATENT DOCUMENTS 3-100463  4/1991  Japan ........................ 33/22

Primary Examiner—Emanuel T. Voeltz
Assistant Examiner—Kyle J. Choi
Attorney, Agent, or Firm—James H. Takemoto

[57] ABSTRACT

A method for predicting the properties of crude oils or their boiling fractions which comprises selecting a chemical or perceptual or physical or performance property or groups of properties of the crude oil or its boiling fractions and creating a training set from reference samples which contain characteristic molecular species present in the crude oil or its boiling fractions. The reference samples are subjected to GC/MS analysis wherein the often collinear data generated is treated by multivariate correlation methods. The training set produces coefficients which are multiplied by the matrix generated from a GC/MS analysis of an unknown sample to produce a predicted value of the chemical, performance, perceptual or physical property or groups of properties selected.

11 Claims, 8 Drawing Sheets

METHOD FOR PREDICTING CHEMICAL OR PHYSICAL PROPERTIES OF CRUDE OILS

BACKGROUND OF THE INVENTION

1. Field of the Invention

This invention relates to a method for rapidly predicting the physical and chemical properties of a crude oil and/or its boiling fractions using a combination of gas chromatography and mass spectrometry.

2. Description of the Related Art

Traditional wet chemistry methods for obtaining physical and chemical properties which define crude oils quality are very time consuming. Crude oils are commonly subjected to distillation and the resultant distillation fractions subjected to numerous analytical and physical test. Crude oils typically contain many thousands of different chemical compounds and therefore only bulk properties for classes of compounds are usually measured, e.g., viscosity, pour point, API gravity and the like.

Gas chromatography has been used to predict physical and performance properties of hydrocarbon mixtures boiling in the gasoline range. Crawford and Hellmuth, Fuel, 1990, 69, 443–447, describe the use of gas chromatography and principal components regression analysis to predict the octane values for gasolines blended from different refinery streams. Japanese laid-open patent application JP 03-100463 relates to a method of estimating the cetane number for fuel oils by separating an oil sample into its components using gas chromatograpy, measuring the signal strength of ion intensities at characteristic masses in the mass spectrum, and correlating these ion intensities to cetane number using multiple regression analysis.

Combined gas chromatography/mass spectrometry (GS/MS) analysis has been done on crude oils. U.S. Pat. No. 5,119,315 discloses a method for aligning sample data such as a mass chromatogram with reference data from a known substance. Williams et al, 12th European Assoc. Organic Geochem., Organic Geochem. Int. Mtg. (Germany 09/16-20/85); Organic Geochemistry 1986, Vol. 10 (1–3) 451–461, discusses the biodegradation of crude oils as measured by GC/MS analysis.

It would be desirable to have a method for rapidly predicting properties of crude oils and/or their boiling fractions using gas chromatography/mass spectrometry which method involves analyzing collinear data.

SUMMARY OF THE INVENTION

This invention relates to a method for predicting physical, performance, perceptual and/or chemical properties of a crude oil which comprises:

(a) selecting at least one property of the crude oil or its boiling fractions;

(b) selecting reference samples, said reference samples containing characteristic compound types present in the crude oil or its boiling fractions and which have known values of the property or properties selected in step (a);

(c) producing a training set by the steps of:

(1) injecting each reference sample into a gas chromatograph which is interfaced to a mass spectrometer thereby causing at least a partial separation of the hydrocarbon mixture into constituent chemical components and recording retention times of the partially separated components;

(2) introducing the constituent chemical components of each reference sample into the mass spectrometer, under dynamic flow conditions;

(3) obtaining for each reference sample a series of time resolved mass chromatograms;

(4) calibrating the retention times to convert them to atmospheric equivalent boiling points;

(5) selecting a series of atmospheric boiling point fractions;

(6) selecting within each boiling point fraction a series of molecular and/or fragment ions, said ions being representative of characteristic compounds or compound classes expected within the boiling point fraction;

(7) (i) recording the total amount of mass spectral ion intensity of each characteristic compound or compound group selected in step c(6), and optionally (ii) multiplying total amounts of mass spectral ion intensities of each characteristic compound or compound group from (7)(i) by weighting factors to produce either weight or volume percent data;

(8) forming the data from steps c(6) and either of c(7)(i) or c(7)(ii) into a X-block matrix;

(9) forming the property data selected in (a) for reference samples selected in (b) into a Y-block matrix;

(10) analyzing the data from steps c(8) and c(9) by multivariate correlation techniques including Partial Least Squares, Principal Component Regression, or Ridge Regression to produce a series of coefficients;

(d) subjecting a crude oil or its boiling fractions to steps c(1) and c(3) in the same manner as the reference samples to produce a series of time resolved mass chromatograms;

(e) repeating steps c(4) to c(8) for each mass chromatogram from step (d);

(f) multiplying the matrix from step (e) by the coefficients from step c(10) to produce a predicted value of the property or properties for the crude oil or its boiling fractions.

The Gas Chromatography/Mass Spectrometry (GC/MS) method described above can be used to predict a wide range of chemical and physical properties (including performance and perceptual properties) of crude oils such as chemical composition and concentration data on specific components, distillation properties, viscosity, pour point, cloud point, octane number, API gravity, and the like in a short time period.

DETAILED DESCRIPTION OF THE INVENTION

Figure 1:
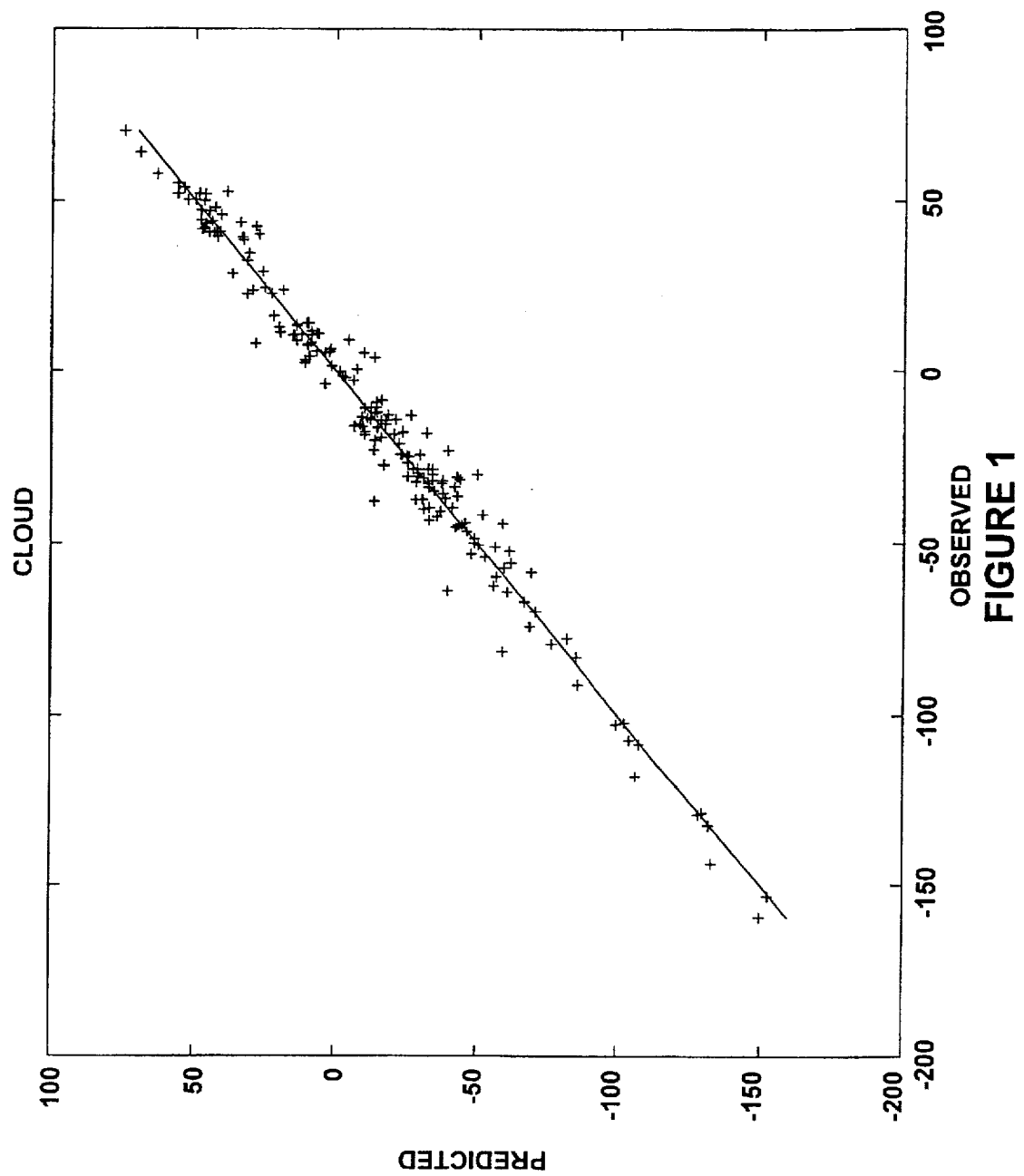
FIG. 1 is a plot of predicted vs. observed values of cloud points for crude oils.

Crude oils contain many thousands of different individual chemical compounds including organic, metallo-organic and inorganic compounds. A complete analysis of crude oil components would be extremely difficult even with modern instrumental techniques. In order to predict bulk properties of a crude oil or its boiling fractions, one must obtain information on key chemical components within different classes of the constituents of crude oils. The more chemical components identified, the better the prediction. However, these additional components greatly increase the data that must be quantitatively treated.

The present method for predicting chemical and physical properties for crude oils involves quantitative identification of components using a combination of retention times from a GC analysis coupled with target fragment and/or molecular ions produced by the MS. The MS information is compared with a set of known properties from reference samples which form a training set. By mathematically comparing the experimental data against that of the training set, one may predict the desired properties of the unknown mixture.

GC/MS utilizes a gas chromatograph interfaced with a mass spectrometer. While a chromatographic method such as supercritical fluid chromatography, liquid chromatography or size exclusion chromatography may be used to separate the mixture into components or mixtures of components, capillary gas chromatography is the preferred means for interfacing with a mass spectrometer. Both GC and MS utilize computer software for instrument control, data acquisition and data reduction.

The sample mixture to be analyzed is first injected into a GC where the mixture components are separated as a function of retention time and boiling point. Only partial chromatographic resolution of mixture components is necessary. The GC oven temperature control is usually programmed for samples with a wide boiling range. Components may also be identified by a detector such as a flame ionization detector, thermal conductivity detector, atomic emission detector or electron capture detector.

The separated or partially separated components are then transferred to the mass spectrometer under dynamic flow conditions. Since a GC operates under atmospheric pressure and a MS under vacuum conditions (about $10^{-3}$ kPa), the instrument interface requires a coupling device such as a molecular separator (e.g., jet, membrane, etc.), open split coupler or capillary direct interface to efficiently transfer sample while minimizing carrier gas effects.

Depending on the nature of the sample, the mixture may be introduced directly into a MS using a direct insertion probe without a prior GC separation step. Other thermal separation techniques not involving a GC may be used to introduce the sample into the mass spectrometer.

In the MS, sample molecules are bombarded with high energy electrons thereby creating molecular ions which fragment in a pattern characteristic of the molecular species involved. A continuous series of mass spectra are obtained over a scan range of 10 or more daltons to at least 800 daltons. The mass spectral data may also be acquired under selected ion monitoring (SIM) mode. In the selected ion mode, care must be taken to select ions representative of the components of interest and to operate under repeatable conditions. A variety of MS instruments may be used including low resolution, high resolution, MS/MS (hybrid, triple quadrupole, etc.), ion cylotron resonance and time of flight. Any ionization technique may be used, such as electron ionization, chemical ionization, multiphoton ionization, field desorption, field ionization, etc., provided that the technique provides either molecular or fragment ions which are suitable for use in the analysis procedure.

The results of sample analysis are a series of l mass spectra. The mass spectra are divided into n time intervals where n is an integer from 1 to l. At least one diagnostic ion is chosen from each of m time intervals where m is an integer from 1 to n. The term "diagnostic ion" refers to an ion which is representative a compound, a chemical class or a physical property correlated thereto. Regardless of whether mass spectra are obtained in the scan or selected ion monitoring mode, it is important that the mass spectra be obtained under repeatable conditions.

If the mass spectral data are acquired in the scan mode, the mass range covered during the mass spectrometer acquisition should be sufficient to provide acquisition of all of the ions which could be used as diagnostic ions during mathematical treatment of each mass spectral scan. If the mass spectral data are acquired in the selected ion monitoring mode, then care must be taken that the ions selected for monitoring are suitable for use in measuring the components of interest.

The sample mass spectral data are then compared to mass spectral data from a series of reference samples with known physical or chemical properties. In order to compare reference mass spectral data with sample mass spectral data, it is desirable to convert sample retention time data to atmospheric equivalent temperature data and also reference sample data to help ensure the integrity of the comparison. There are commercially available computer program available for such data alignment, for example, Hewlett-Packard GC/MS Software G1034C version C.01.05.

The reference mass spectral data, and associated properties data, are arranged in matrix form for mathematical treatment as described below. In the case of chemical composition information, one matrix is formed of reference sample ion intensities at given masses and the other matrix contains known ion intensities for molecular fragment ions of known components. The training set for chemical composition data is thus made up of mass spectral data for different components characteristic of components expected to be found in the sample mixtures. Similar training sets can be formed for other chemical or perceptual or performance or physical properties of interest. These training sets form one block or matrix of data (Y-block or properties matrix). The actual sample mass spectral data (which may have been temperature aligned) form the other block (X-block) or matrix of data. These two matrices are subjected to mathematical treatment known as Partial Least Squares (PLS), or Principal Component Regression (PCR), or Ridge Regression (RR) to obtain a mathematically describable relationship between the properties data and mass spectral data, known as a model. Coefficients provided by this model are mathematically combined with the suitably treated mass spectral data from samples with unknown desired properties to:

a) predict desired properties, b) assess the suitability of the model for such predictions, and c) diagnose the stability and general correctness of the process that yielded the mass spectral data.

PLS/PCR/RR are described in the literature, e.g., Wold S., A. Ruhe, H. Wold, and W. J. Dunn, "The Collinearity Problem in Linear Regression. The Partial Least Squares (PLS) Approach to Generalized Inverses", SIAM J. Sci. Stat. Comput., 1984 5(3), 735–743, or Geladi P., and B. R. Kowalki, "Partial Least Squares Regression: A Tutorial", Anal. Chim. Acta, 1986, 185, 1–17, or Hökuldsson A., "PLS Regression Methods", J. Chemometrics, 1988, 2, 211–228, or in many other articles in journals such as the Journal of Chemometrics or Intelligent Laboratory Systems; Frank, I. and J. Friedman, "A Statistical View of Some Chemometrics Regression Tools", Technometrics, 1993, Vol. 35, No. 2; Jackson, J. E., "A User's Guide To Principal Components", Wiley-Interscience, New York, 1991; Montgomery, D. C. and E. A. Peck, "Introduction To Linear Regression Analysis", Wiley-Interscience, New York, 1990; and Martens, H., and T. Naes, "Multi-variable Calibration", Wiley-Interscience, New York, 1989.

When dealing with a complex mixture, it is necessary to select appropriate masses or groups of masses at specific retention times for a particular compound or classes of compounds. This may be accomplished by either Hydrocarbon Compound Type Analysis or Chemist's Rules. For crude oils, it is preferred to use Hydrocarbon Compound Type Analysis. However, Chemist's Rules may be used and the selection of such masses is the basis for a set a rules which then forms the data for the training set. There are no set procedures for such a selection process. The researcher must select appropriate masses for These coefficients are then multiplied by the data matrix for the sample. The result is a prediction of the desired property or properties. The method of the invention is further illustrated by the following examples.

EXAMPLE 1

The method for predicting the physical or chemical properties for a range of boiling fractions of crude oils is demonstrated in this example using API gravity of crude oil fractions as the specific property for purposes of illustration. The method is generally applicable to a range of other physical properties as well as chemical, perceptual or performance properties of such mixtures, such as saturates and aromatics content, smoke point, pour point, viscosity, etc.

The initial consideration is to establish a set of standard GC/MS operating parameters so that the GC/MS analytical data used for predicting properties are obtained under consistent operating conditions. The GC/MS instrument used in this example is a Hewlett-Packard 5970 Mass Selective Detector interfaced to a Hewlett-Packard 5890 Series II Gas Chromatograph.

The GC/MS operating conditions are summarized in Table 1.

| GC Conditions | |
|---|---|
| Column | Fused silica capillary column such as J&W DB 1 HT: 15 m × 0.25 mm, 0.1 micron film thickness |
| Temperature Program | |
| Initial Temperature (°C.) | −40 |
| Initial Time (minutes) | 0 |
| Program Rate (°C./minute) | 10 |
| Final Temperature (°C.) | 380 |
| Final Time (minutes) | 18 |
| Carrier Gas | Helium |
| Injection Volume μL | 0.5 |
| Split Ratio | 5:1 |
| Column Head Press, psi | Approx. 2 |
| Interface Temperature (°C.) | 300 |
| Mass Spectrometer Conditions | |
| Ionization Mode | Electron Ionization, 70 eV nominal |
| Mass Range Scanned (daltons) | 10–800 |
| scan/sec | 1.56 |

A Gerstel injector was used to introduce the sample without discrimination and simultaneously maintain vacuum-tight seals throughout the system during the analysis. The injector was programmed at a fast, controllable rate (12° C./sec) from −150° C. to 400° C. A dilute solution (about 2%) of sample in $CS_2$ was introduced with an autosampler.

In order to predict properties of an unknown hydrocarbon mixture, it is first necessary to select reference samples having known values of the property or properties to form a model training set. In this example, a suite of 46 crude oils were used, covering a broad range of API gravity as shown in Table 2.

TABLE 2

| COUNTRY | API GRAVITY |
|---|---|
| U.S.A. - 1 | 29.00 |
| Nigeria - 1 | 32.10 |
| Saudi Arabia - 1 | 32.50 |
| Saudi Arabia - 2 | 27.30 |
| Saudi Arabia - 3 | 32.50 |
| Saudi Arabia - 4 | 30.40 |
| Abu Dhabi - 1 | 43.50 |
| Venezuela | 22.00 |
| Chad - 1 | 21.80 |
| Nigeria - 2 | 43.10 |
| Angola | 32.70 |
| Australia | 39.70 |
| Dubai | 31.90 |
| U.S.A. - 1 | 29.00 |
| Nigeria - 1 | 32.10 |
| Saudi Arabia - 1 | 32.50 |
| Saudi Arabia - 2 | 27.30 |
| Saudi Arabia - 3 | 32.50 |
| Saudi Arabia - 4 | 30.40 |
| Abu Dhabi - 1 | 43.50 |
| Venezuela | 22.00 |
| Chad - 1 | 21.80 |
| Nigeria - 2 | 43.10 |
| Angola | 32.70 |
| Australia | 39.70 |
| Dubai | 31.90 |
| Denmark | 33.20 |
| U.K. | 23.10 |
| Nigeria - 3 | 36.50 |
| Nigeria - 4 | 29.10 |
| U.S.A. - 2 | 29.60 |
| U.S.A. - 3 | 33.80 |
| Kuwait - 1 | 31.90 |
| U.S.A. - 4 | 21.90 |
| Egypt | 30.00 |
| Norway | 33.50 |
| U.S.A. - 5 | 19.00 |
| U.S.A. - 6 | 19.40 |
| Iran | 34.20 |
| Chad - 2 | 17.20 |
| Kuwait - 2 | 31.90 |
| Cameroon | 21.10 |
| Yemen - 1 | 44.70 |
| Yemen - 2 | 47.80 |
| Yemen - 3 | 31.00 |
| Chad - 3 | 24.60 |
| Abu Dhabi - 2 | 40.40 |
| Abu Dhabi - 3 | 39.50 |
| Nigeria - 5 | 27.90 |
| Mexico | 38.50 |
| Oman | 34.20 |
| U.S.A. - 7 | 45.00 |
| Gabon | 33.70 |
| Russia - 1 | 28.10 |
| Algeria | 43.30 |
| Russia - 2 | 32.60 |
| Syria | 36.20 |
| U.S.A. - 8 | 18.00 |
| Malaysia | 47.00 |

A data treatment method should be selected prior to obtaining raw GC/MS data. Two types of data treatments which may be used are Chemist's Rules and Hydrocarbon Compound Type Analysis as described, for example, in Robinson, C. J., "Low Resolution Determination of Aromatics and Saturates in Petroleum Fractions", Analytical Chemistry, 43(11), 1425–1434 (1971). The data treatment procedures involve two separate sections: (1) a calibration section to convert the retention time axis to the boiling point axis; and (2) the actual Hydrocarbon Compound Type Analysis or the Chemist's Rules which are based on a selected series of masses and correspond to prominent compounds or compound types expected for the type of hydrocarbon mixture under investigation. These compounds or compound types are selected on the basis that they have prominent molecular and/or fragment ions unique to that compound or molecular series. A portion of a set of the Chemist's Rules are shown in Table 3.

concerning the specific interval or intervals. The retention time to boiling point calibration accounts for slight shifts in retention times which may result from column degradation, column head pressure fluctuations, changes in column carrier gas linear velocity, or minor fluctuations in the GC column oven temperatures or other causes. Hydrocarbon

TABLE 3

| RULES[a] | COMPOUND[b] | Mass[c] | | | | | | RETENTION TIME[d] START | END |
|---|---|---|---|---|---|---|---|---|---|
| 1 | Paraffins | 43 | 57 | 71 | 85 | 99 | 113 | 0.400 | 3.162 |
| 2 | Cycloparaffins | 41 | 55 | 69 | 83 | 97 | 111 | 0.400 | 3.162 |
| 3 | Toluene | 91 | 92 | | | | | 0.400 | 2.860 |
| 4 | $C_nH_{2n-8}$ | 117 | 131 | 145 | 159 | 163 | 177 | 2.851 | 3.162 |
| 5 | $C_nH_{2n-6}$ | 91 | 105 | 119 | 133 | 147 | 161 | 2.851 | 3.162 |
| 6 | $C_nH_{2n-12}$ | 141 | 155 | 169 | 183 | 197 | 211 | 2.851 | 3.162 |
| 7 | $C_nH_{2n-10}$ | 115 | 129 | 143 | 157 | 171 | 185 | 2.851 | 3.162 |
| 8 | $C_nH_{2n-18}$ | 178 | 191 | 205 | 219 | 233 | 247 | 2.851 | 3.162 |
| 9 | n-C8 | 43 | 57 | 71 | 85 | 99 | 114 | 3.162 | 3.200 |
| 10 | i-Paraffins | 43 | 57 | 71 | 85 | 99 | 113 | 3.200 | 4.100 |
| 11 | Cycloparaffins | 41 | 55 | 69 | 83 | 97 | 111 | 3.200 | 4.100 |
| 12 | $C_nH_{2n-8}$ | 117 | 131 | 145 | 159 | 163 | 177 | 3.200 | 4.100 |
| 13 | $C_nH_{2n-6}$ | 91 | 105 | 119 | 133 | 147 | 161 | 3.200 | 4.100 |
| 14 | $C_nH_{2n-12}$ | 141 | 155 | 169 | 183 | 197 | 211 | 3.200 | 4.100 |
| 15 | $C_nH_{2n-10}$ | 115 | 129 | 143 | 157 | 171 | 185 | 3.200 | 4.100 |
| 16 | $C_nH_{2n-18}$ | 178 | 191 | 205 | 219 | 233 | 247 | 3.200 | 4.100 |
| • | • | • | • | • | • | • | • | • | • |
| • | • | • | • | • | • | • | • | • | • |
| • | • | • | • | • | • | • | • | • | • |
| 137 | n-C24 | 43 | 57 | 71 | 85 | 99 | 338 | 10.912 | 10.964 |
| 138 | i-Paraffins | 43 | 57 | 71 | 85 | 99 | 113 | 10.964 | 14.800 |
| 139 | Cycloparaffins | 41 | 55 | 69 | 83 | 97 | 111 | 10.964 | 14.800 |
| 140 | $C_nH_{2n-8}$ | 117 | 131 | 145 | 159 | 163 | 177 | 10.964 | 14.800 |
| 141 | $C_nH_{2n-6}$ | 91 | 105 | 119 | 133 | 147 | 161 | 10.964 | 14.800 |
| 142 | $C_nH_{2n-12}$ | 141 | 155 | 169 | 183 | 197 | 211 | 10.964 | 14.800 |
| 143 | $C_nH_{2n-10}$ | 115 | 129 | 143 | 157 | 171 | 185 | 10.964 | 14.800 |
| 144 | $C_nH_{2n-18}$ | 178 | 191 | 205 | 219 | 233 | 247 | 10.964 | 14.800 |

[a]Rule number, integer index
[b]Compound or group of compounds rule applies to
 cycloparaffins   alkylated 1 ring cycloparaffins
 $C_nH_{2n-6}$    alkylated benzenes
 $C_nH_{2n-8}$    alkylated indanes
 $C_nH_{2n-10}$   alkylated indenes
 $C_nH_{2n-12}$   alkylated naphthalenes
 $C_nH_{2n-18}$   alkylated phenanthrenes/anthracenes
[c]Masses used in Rule [up to n may be specified, where n is an integer which is equal to the number of masses scanned during the time interval (d) either in full scan mode or selected ion monitoring mode].
[d]Retention time for both starting and ending expected retention times based on historical averages in minutes.

A calibration table based on standard curve-fitting mathematical procedures is used to establish relationships between the measured retention times and the known boiling points of a standard mixture of n-alkanes covering the carbon number range: $C_5$ to higher than $C_{60}$. Table 4 displays a typical calibration table containing the retention times of the n-alkanes and their known boiling points. A similar calibration can be performed using the inherent information of the hydrocarbon compounds identified by their mass spectra in the mass chromatogram of the sample and their known boiling points. In that manner, all mass chromatographic information obtained in the retention time axis is converted to the boiling point axis. Hydrocarbon Compound Type Analysis or Chemist's Rules procedures are applied to pre-selected boiling point intervals or fractions. These boiling point intervals are specified by the user. It is also possible to use a combination of Hydrocarbon Type Analysis and Chemist's Rules wherein Hydrocarbon Type Analysis is applied to the boiling point intervals and Chemist's Rules are applied within one or more of the intervals. This type of treatment provides more detailed information concerning the specific interval or intervals. Compound Type Analysis is preferred as this method reduces the amount of data to be treated. Since one is usually concerned with bulk properties of crude oils, compound types within selected boiling intervals provide sufficient data to permit prediction of these properties.

TABLE 4

| Carbon Number | Retention Time (min) | Boiling Point (C) |
|---|---|---|
| 5 | 1.415 | 36 |
| 6 | 3.029 | 69 |
| 7 | 4.497 | 98 |
| 8 | 6.281 | 126 |
| 9 | 8.05 | 151 |
| 10 | 9.677 | 174 |
| 11 | 11.21 | 196 |
| 12 | 12.6 | 216 |
| 14 | 15.19 | 254 |
| 15 | 16.359 | 271 |
| 16 | 17.511 | 287 |

TABLE 4-continued

| Carbon Number | Retention Time (min) | Boiling Point (C) |
|---|---|---|
| 17 |  | 302 |
| 18 | 19.564 | 316 |
| 20 | 21.443 | 344 |
| 22 |  | 369 |
| 24 | 24.792 | 391 |
| 26 | 26.262 | 412 |
| 28 | 27.684 | 431 |
| 30 | 28.933 | 449 |
| 32 | 30.197 | 466 |
| 34 | 31.320 | 481 |
| 36 | 32.458 | 496 |
| 38 | 33.454 | 509 |
| 40 | 34.498 | 522 |
| 42 | 35.415 | 534 |
| 44 | 36.381 | 545 |
| 46 | 37.283 | 556 |
| 48 | 38.249 | 567 |
| 50 | 39.247 | 576 |
| 52 | 40.245 | 585 |
| 54 | 41.737 | 594 |

TABLE 4-continued

| Carbon Number | Retention Time (min) | Boiling Point (C) |
|---|---|---|
| 56 | 43.211 | 601 |
| 58 | 44.431 | 608 |
| 60 | 46.120 | 615 |

Once the conversion of the retention time axis to the boiling point axis is accomplished, the Hydrocarbon Compound Type Analysis or Chemist's Rules are applied to the raw mass spectrometric data. Typical user-specified boiling point intervals with their corresponding end points are shown on Table 5. Mass spectrometric information is derived for these intervals using Hydrocarbon Compound Type Analysis or Chemist's Rules. Typical information obtained with the Hydrocarbon Compound Type Analysis for a crude oil is shown in Table 5.

TABLE 5

| End Boiling pt. (deg C.) | 85 | 88 | 100 | 125 | 150 | 175 | 205 | 220 | 235 | 265 | 295 |
|---|---|---|---|---|---|---|---|---|---|---|---|
| Retention time (min) | 3.8 | 3.85 | 4.4 | 5.85 | 7.7 | 9.55 | 11.55 | 13.15 | 14.25 | 15.85 | 18 |
| Weight Percent | 2.33 | 0.27 | 2.71 | 5.12 | 4.79 | 4.98 | 5.4 | 2.77 | 2.73 | 5.1 | 5.15 |
| Paraffins | 0.5 | 0.06 | 2.34 | 3.46 | 2.97 | 3.06 | 3.08 | 1.83 | 1.58 | 2.33 | 2.2 |
| 1-ring cycloparaffins | 1.7 | 0.2 | 0.35 | 1.07 | 0.97 | 0.84 | 0.95 | 0.38 | 0.46 | 0.85 | 0.97 |
| 2-ring cycloparaffins | 0 | 0 | 0 | 0 | 0.06 | 0.15 | 0.28 | 0.19 | 0.19 | 0.38 | 0.36 |
| 3-ring cycloparaffins | 0 | 0 | 0 | 0 | 0.01 | 0 | 0 | 0.02 | 0.04 | 0.24 | 0.25 |
| Alkylbenzenes | 0 | 0 | 0 | 0.58 | 0.67 | 0.91 | 1.05 | 0.23 | 0.22 | 0.4 | 0.33 |
| Naphthenebenzenes | 0 | 0 | 0 | 0 | 0 | 0 | 0.01 | 0.09 | 0.13 | 0.3 | 0.22 |
| Dinaphthenebenzenes | 0 | 0 | 0 | 0 | 0 | 0 | 0 | 0 | 0.01 | 0.06 | 0.15 |
| Naphthalenes | 0 | 0 | 0 | 0 | 0 | 0.01 | 0.03 | 0.01 | 0.09 | 0.29 | 0.4 |
| Acenaphthene/Dibenzofurans | 0 | 0 | 0 | 0 | 0 | 0 | 0 | 0 | 0 | 0 | 0.04 |
| Fluorenes | 0.01 | 0 | 0 | 0 | 0 | 0 | 0 | 0 | 0 | 0.02 | 0.03 |
| Phenanthrenes | 0 | 0 | 0 | 0 | 0 | 0 | 0 | 0 | 0 | 0 | 0 |
| Naphthenephenanthrenes | 0.1 | 0.01 | 0.01 | 0 | 0 | 0 | 0 | 0 | 0 | 0 | 0 |
| Pyrenes | 0 | 0 | 0 | 0 | 0.01 | 0 | 0 | 0 | 0 | 0 | 0 |
| Chrysenes | 0.01 | 0 | 0 | 0 | 0 | 0 | 0 | 0 | 0 | 0 | 0 |
| Perylenes | 0 | 0 | 0 | 0 | 0 | 0 | 0 | 0 | 0 | 0 | 0 |
| Dibenzanthracenes | 0 | 0 | 0 | 0 | 0 | 0 | 0 | 0 | 0 | 0 | 0 |
| Benzothiophenes | 0 | 0 | 0 | 0 | 0 | 0 | 0 | 0.01 | 0.02 | 0.13 | 0.19 |
| Dibenzothiophenes | 0 | 0 | 0 | 0 | 0.02 | 0 | 0 | 0 | 0 | 0 | 0 |
| Naphthobenzothiophenes | 0 | 0 | 0 | 0 | 0 | 0 | 0 | 0 | 0 | 0 | 0 |
| Cn.H2n-36/Cn.H2n-26.S | 0 | 0 | 0 | 0 | 0.08 | 0 | 0 | 0 | 0 | 0 | 0 |
| Cn.H2n-38/Cn.H2n-28.S | 0 | 0 | 0 | 0 | 0 | 0 | 0 | 0 | 0 | 0 | 0 |
| Cn.H2n-26 | 0 | 0 | 0 | 0 | 0 | 0 | 0 | 0 | 0 | 0 | 0 |
| Cn.H2n-42/Cn.H2n-32.S | 0 | 0 | 0 | 0 | 0 | 0 | 0 | 0 | 0 | 0 | 0 |
| Cn.H2n-44/Cn.H2n-34.S | 0.01 | 0 | 0 | 0 | 0 | 0 | 0 | 0 | 0 | 0 | 0 |
| Cn.H2n-32 | 0 | 0 | 0 | 0 | 0 | 0 | 0 | 0 | 0 | 0 | 0.01 |
| Total Saturates | 2.2 | 0.28 | 2.89 | 4.54 | 4.01 | 4.05 | 4.31 | 2.42 | 2.26 | 3.9 | 3.78 |
| Monoaromatics | 0 | 0 | 0 | 0.56 | 0.67 | 0.81 | 1.06 | 0.32 | 0.36 | 0.76 | 0.69 |
| Diaromatics | 0.01 | 0 | 0 | 0 | 0 | 0.02 | 0.03 | 0.01 | 0.09 | 0.31 | 0.47 |
| Triaromatics | 0.1 | 0.01 | 0.01 | 0 | 0 | 0 | 0 | 0 | 0 | 0 | 0 |
| Tetraaromatics | 0.01 | 0 | 0 | 0 | 0.01 | 0 | 0 | 0 | 0 | 0 | 0 |
| Pentaaromatics | 0 | 0 | 0 | 0 | 0 | 0 | 0 | 0 | 0 | 0 | 0 |
| Thiophenoaromatics | 0 | 0 | 0 | 0 | 0.02 | 0 | 0 | 0.01 | 0.02 | 0.13 | 0.19 |
| Unidentified Aromatics | 0.01 | 0 | 0.01 | 0 | 0.08 | 0 | 0 | 0 | 0 | 0 | 0.01 |
| Total Aromatics | 0.13 | 0.02 | 0.02 | 0.58 | 0.79 | 0.94 | 1.09 | 0.35 | 0.47 | 1.2 | 1.37 |

| End Boiling pt. (deg C.) | 320 | 345 | 400 | 427 | 455 | 483 | 510 | 537 | 565 | 593 |
|---|---|---|---|---|---|---|---|---|---|---|
| Retention time (min) | 19.95 | 21.7 | 24.65 | 27.75 | 29.9 | 32.1 | 34.3 | 36.6 | 39.05 | 41.65 |
| Weight Percent | 3.84 | 3.92 | 8.34 | 3.94 | 3.88 | 3.62 | 3.36 | 3.38 | 3.19 | 3.08 |
| Paraffins | 1.57 | 1.16 | 2.12 | 0.71 | 0.49 | 0.33 | 0.15 | 0.01 | 0 | 0 |
| 1-ring cycloparaffins | 0.73 | 0.73 | 1.44 | 0.84 | 0.82 | 0.55 | 0.49 | 0.45 | 0.35 | 0.08 |
| 2-ring cycloparaffins | 0.26 | 0.33 | 0.61 | 0.29 | 0.35 | 0.27 | 0.3 | 0.11 | 0.13 | 0.07 |
| 3-ring cycloparaffins | 0.18 | 0.21 | 0.47 | 0.29 | 0.41 | 0.47 | 0.53 | 0.81 | 0.53 | 0.18 |
| Alkylbenzenes | 0.25 | 0.29 | 0.49 | 0.19 | 0.18 | 0.14 | 0.14 | 0.13 | 0.09 | 0 |
| Naphthenebenzenes | 0.12 | 0.15 | 0.33 | 0.16 | 0.17 | 0.21 | 0.14 | 0.14 | 0.07 | 0 |

TABLE 5-continued

| | | | | | | | | | | |
|---|---|---|---|---|---|---|---|---|---|---|
| Dinaphthenebenzenes | 0.13 | 0.15 | 0.3 | 0.18 | 0.16 | 0.19 | 0.21 | 0.16 | 0.15 | 0.09 |
| Naphthalenes | 0.18 | 0.29 | 0.19 | 0.1 | 0.12 | 0.11 | 0.07 | 0.05 | 0.03 | 0 |
| Acenaphthene/Dibenzofurans | 0.09 | 0.14 | 0.3 | 0.18 | 0.15 | 0.14 | 0.15 | 0.16 | 0.17 | 0.19 |
| Fluorenes | 0.06 | 0.13 | 0.39 | 0.2 | 0.18 | 0.19 | 0.2 | 0.33 | 0.64 | 1.45 |
| Phenanthrenes | 0.02 | 0.11 | 0.23 | 0.08 | 0.09 | 0.08 | 0.04 | 0.01 | 0 | 0 |
| Naphthenephenanthrenes | 0 | 0.03 | 0.17 | 0.13 | 0.14 | 0.15 | 0.04 | 0.01 | 0 | 0 |
| Pyrenes | 0.01 | 0.04 | 0.2 | 0.18 | 0.11 | 0.08 | 0.08 | 0.06 | 0.02 | 0 |
| Chrysenes | 0 | 0.01 | 0.07 | 0.05 | 0.1 | 0.05 | 0.04 | 0.06 | 0.09 | 0.14 |
| Perylenes | 0 | 0 | 0 | 0.04 | 0.03 | 0.07 | 0.06 | 0.08 | 0.05 | 0.05 |
| Dibenzanthracenes | 0 | 0 | 0.01 | 0.01 | 0.01 | 0.02 | 0.03 | 0.04 | 0.02 | 0 |
| Benzothiophenes | 0.14 | 0.15 | 0.35 | 0.17 | 0.18 | 0.17 | 0.17 | 0.17 | 0.13 | 0 |
| Dibenzothiophenes | 0.1 | 0 | 0.64 | 0.15 | 0.12 | 0.1 | 0.13 | 0.12 | 0.1 | 0.07 |
| Naphthobenzothiophenes | 0 | 0 | 0.04 | 0.13 | 0.13 | 0.1 | 0.1 | 0.07 | 0.05 | 0.01 |
| Cn.H2n-36/Cn.H2n-26.S | 0 | 0 | 0 | 0 | 0.07 | 0.05 | 0 | 0 | 0 | 0 |
| Cn.H2n-38/Cn.H2n-28.S | 0 | 0 | 0 | 0 | 0 | 0.04 | 0 | 0.02 | 0.02 | 0 |
| Cn.H2n-26 | 0 | 0 | 0 | 0.09 | 0.1 | 0.09 | 0.18 | 0.23 | 0.38 | 0.73 |
| Cn.H2n-42/Cn.H2n-32.S | 0 | 0 | 0 | 0 | 0 | 0 | 0.03 | 0.08 | 0.04 | 0 |
| Cn.H2n-44/Cn.H2n-34.S | 0 | 0 | 0 | 0 | 0 | 0 | 0 | 0.01 | 0.01 | 0 |
| Cn.H2n-32 | 0 | 0 | 0 | 0 | 0 | 0.03 | 0.08 | 0.11 | 0.12 | 0.03 |
| Total Saturates | 2.74 | 2.44 | 4.84 | 1.93 | 1.87 | 1.82 | 1.47 | 1.38 | 1.01 | 0.33 |
| Monoaromatics | 0.5 | 0.58 | 1.11 | 0.53 | 0.51 | 0.54 | 0.49 | 0.43 | 0.32 | 0.09 |
| Diaromatics | 0.33 | 0.55 | 0.88 | 0.46 | 0.44 | 0.44 | 0.42 | 0.54 | 0.84 | 1.64 |
| Triaromatics | 0.02 | 0.14 | 0.4 | 0.22 | 0.24 | 0.23 | 0.07 | 0.02 | 0 | 0 |
| Tetraaromatics | 0.01 | 0.05 | 0.27 | 0.22 | 0.21 | 0.11 | 0.13 | 0.12 | 0.11 | 0.14 |
| Pentaaromatics | 0 | 0 | 0.01 | 0.05 | 0.04 | 0.09 | 0.09 | 0.1 | 0.06 | 0.05 |
| Thiophenoaromatics | 0.24 | 0.15 | 1.03 | 0.45 | 0.41 | 0.37 | 0.4 | 0.35 | 0.28 | 0.08 |
| Unidentified Aromatics | 0 | 0 | 0 | 0.09 | 0.17 | 0.21 | 0.29 | 0.43 | 0.57 | 0.76 |
| Total Aromatics | 1.1 | 1.48 | 3.7 | 2.01 | 2.01 | 2 | 1.89 | 2 | 2.18 | 2.78 |

The analysis summarized in Table 5 is done for each reference sample. The results from these respective analyses form a training set which is subjected to mathematical treatment. The goal is to develop a model that can be used to predict the unknown properties of future samples using their mass spectral data only. The mathematical treatments are described by multivariate correlation techniques such as Projection to Latent Structures (PLS) or otherwise known as Partial Least Squares (PLS), Principal Component Regression (PCR), and Ridge Regression (RR). These techniques are superior to ordinary multiple linear regression in their ability to treat collinearity amongst variables in the X-block or GC/MS data matrix (and Y-block or properties matrix for PLS), and in their ability to handle the quantity of data generated by the analysis of crude oils. Ordinary Multiple Linear Regression cannot be used to treat collinear variables.

PLS/PCR/RR are numerical analysis techniques for detecting and formulating a mathematical structure (model) within a data set comprising observations associated with multiple objects. Each object has associated with it observations for multiple variables, the latter being common to all objects. These multiple variables are assigned into two categories, known as X-block and Y-block. Observations associated with all variables in the X-block are realized from a common process (GC/MS data in this case). Observations associated with variables in the Y-block (known properties in this case) are realized from processes that may be different for each variable. The data set used to construct this mathematical model is referred to as the model calibration data set.

The common use of PLS/PCR/RR is to apply the model developed from the calibration data set to X-block observations realized for new objects (not in the calibration data set) to predict values for the corresponding variables in the Y-block for these new objects, without having to execute the Y-block processes used in the calibration data set. Using diagnostics that are simultaneously generated by the PLS/PCR/RR model, assessment of whether the new objects can be adequately described by the model, and whether the model is used in an extrapolation mode versus interpolation mode can be performed.

PLS/PCR addresses the collinearity features in the X-block and Y-block, by suitably reducing the dimensionality in both X- and Y-blocks (for PLS), and X-block only (for PCR) to form the model. Collinearity is a term referring to the existence of relationships between variables within the block itself. In the PLS modeling algorithm a number of independent dimensions in the X- and Y-blocks are identified by forming pseudo-variables known as principal components or latent vectors through different sets of linear combinations of original variables in each block. Each set of such combinations constitutes an independent dimension. It comprises a set of coefficients that each value associated with each variable in the block is to be weighted by to arrive at the new value for this dimension. The values for the new, reduced dimensions in the Y-block are regressed onto their counterparts in the new, reduced dimensions of the X-block to arrive at the most parsimonious dimension size (number of latent vectors) and their associated weights, with the final goal of one linear equation generated to permit prediction of Y-block variables using X-block variables. The number of dimensions used to construct the model is determined through optimization of a criterion known as PRESS (Prediction Error Sum of Squares), cumulated by a Cross Validation (CV) technique using the training data set, and, following the general model parsimony principle.

For PCR, the number of independent dimensions in the X-block are first selected and identified in a similar fashion as in PLS by forming principal components. Then, for each variable in the Y-block, a model is obtained by performing ordinary multiple linear regression using the Principal Components as "Prediction Variables".

For Ridge Regression, the collinearity problem is dealt with in a different manner than PLS/PCR. Here a diagonal matrix known as the Lambda Matrix is added to the Covariance Matrix of the X-block with the net effect of stabilizing the numerical computation needed to obtain the model coefficients. The selection of Lambda values is through optimization of PRESS criterion using cross validation of the training set.

Thus, the Chemist's Rules or Hydrocarbon Types data for the various reference samples derived from GC/MS analysis form the X-block variables. PLS/PCR/RR treatment may require preliminary reorganization of the X-block data, such as transposition and removal of redundant data and constants or mathematical transformations. The Y-block variables are the property (or properties) to be predicted, and may also require mathematical transformations such as logarithmic or geometric, as well as reorganization. The data blocks may be represented by:

X-Block Matrix

[Molecular Types Analysis (n samples×20 columns)]

$$\begin{vmatrix} X_{1,1} & X_{1,2} & X_{1,3} & \cdots & X_{1,18} & X_{1,19} & X_{1,20} \\ X_{2,1} & X_{2,2} & X_{2,3} & \cdots & X_{2,18} & X_{2,19} & X_{2,20} \\ X_{3,1} & X_{3,2} & X_{3,3} & \cdots & X_{3,18} & X_{3,19} & X_{3,20} \\ \cdot & \cdot & \cdot & \cdots & \cdot & \cdot & \cdot \\ \cdot & \cdot & \cdot & \cdots & \cdot & \cdot & \cdot \\ \cdot & \cdot & \cdot & \cdots & \cdot & \cdot & \cdot \\ X_{n,1} & X_{n,2} & X_{n,3} & \cdots & X_{n,18} & X_{n,19} & X_{n,20} \end{vmatrix}$$

Y-Block Matrix

[Measured Property or Properties (n samples)]

$$\begin{vmatrix} Y_1 \\ Y_2 \\ Y_3 \\ \cdot \\ \cdot \\ \cdot \\ Y_n \end{vmatrix}$$

The Y-block may be a single observation per set of Hydrocarbon Type Compound Type analysis as shown above, or it may be a n×m matrix of observations, where there are m different properties to be predicted.

The results of the PLS/PCR/RR treatment of the training set data are a series of coefficients. Compound type data from an unknown sample (or samples) are then treated in the same way as the X-block matrix in the training set, and the coefficients applied to generate the prediction of the desired property or properties. Table 6 illustrates the quality of predicted API gravity for each sample in the training set. The data are presented in sets of three, one set for each of the crudes listed in Table 2: the first pair of columns represents the value for API gravity for the 257°–302° F. boiling range, the second pair 428°–455° F., and the third pair for a residuum beyond 1049° F.

TABLE 6

| Measured* 257–302° F. | Predicted | Measured* 428–455° F. | Predicted | Measured* 1049+° F. | Predicted |
|---|---|---|---|---|---|
| 50.87 | 51.53 | 52.90 | 53.43 | 57.08 | 56.80 |
| 58.22 | 57.77 | 54.55 | 56.90 | 56.90 | 56.17 |
| 53.80 | 53.33 | 53.90 | 55.40 | 41.88 | 45.64 |
| 51.73 | 52.09 | 55.33 | 53.69 | 51.85 | 53.15 |
| 54.71 | 54.95 | 50.28 | 52.10 | 47.72 | 47.44 |
| 50.72 | 50.57 | 48.69 | 47.93 | 54.08 | 54.25 |
| 52.70 | 53.98 | 55.90 | 56.12 | 50.80 | 52.70 |
| 54.43 | 54.92 | 50.97 | 53.11 | 52.18 | 52.52 |
| 53.34 | 52.99 | 53.82 | 54.39 | 53.17 | 47.04 |

TABLE 6-continued

| Measured* 257–302° F. | Predicted | Measured* 428–455° F. | Predicted | Measured* 1049+° F. | Predicted |
|---|---|---|---|---|---|
| 55.90 | 56.72 | 49.63 | 50.46 | 52.26 | 52.25 |
| 52.50 | 51.99 | 56.87 | 55.08 | 53.17 | 48.09 |
| 54.46 | 54.73 | 55.29 | 55.40 | 49.91 | 49.42 |
| 54.69 | 54.13 | 57.87 | 56.04 | 53.44 | 53.13 |
| 51.10 | 52.73 | 55.70 | 52.70 | 56.47 | 54.80 |
| 54.19 | 54.70 | 54.48 | 55.56 | 51.76 | 52.70 |
| 54.51 | 54.42 | 36.38 | 36.96 | 39.11 | 39.08 |
| 42.76 | 43.38 | 43.36 | 42.81 | 42.21 | 42.37 |
| 41.93 | 41.94 | 42.93 | 42.84 | 38.53 | 39.59 |
| 31.77 | 30.78 | 39.95 | 39.90 | 41.14 | 40.54 |
| 40.44 | 39.46 | 40.54 | 39.90 | 34.58 | 36.95 |
| 31.48 | 31.09 | 36.65 | 37.18 | 33.79 | 32.96 |
| 38.55 | 37.69 | 39.10 | 40.04 | 43.47 | 42.45 |
| 35.09 | 37.68 | 40.44 | 40.58 | 37.96 | 38.92 |
| 37.09 | 36.43 | 37.18 | 38.12 | 42.18 | 41.30 |
| 28.68 | 29.30 | 43.47 | 42.82 | 33.37 | 33.77 |
| 40.58 | 40.48 | 40.54 | 39.76 | 40.65 | 40.38 |
| 32.53 | 32.83 | 43.35 | 43.36 | 41.64 | 42.88 |
| 32.85 | 32.72 | 40.83 | 40.77 | 43.37 | 42.52 |
| 42.93 | 44.04 | 43.00 | 42.23 | 40.05 | 37.68 |
| 44.57 | 43.12 | 39.39 | 39.41 | 41.39 | 42.12 |
| 36.70 | 36.53 | 44.11 | 44.98 | 6.20 | 7.44 |
| 6.20 | 7.69 | 7.50 | 6.26 | 3.50 | 3.48 |
| 6.40 | 4.48 | 5.50 | 5.65 | 10.50 | 12.63 |
| 4.20 | 6.66 | 17.30 | 18.70 | 10.20 | 11.36 |
| 13.40 | 15.22 | 5.70 | 7.69 | 4.10 | 4.37 |
| 12.90 | 9.53 | 13.60 | 14.11 | 12.40 | 10.52 |
| 10.20 | 10.26 | 10.00 | 9.76 | 12.40 | 12.19 |
| 5.20 | 5.06 | 4.74 | 4.46 | 5.70 | 6.52 |
| 12.30 | 12.12 | 1.89 | 2.38 | 1.83 | 0.59 |
| 6.00 | 9.41 | 14.90 | 13.91 | 5.20 | 6.81 |
| 5.60 | 4.46 | 11.30 | 12.21 | 11.35 | 10.81 |
| 7.60 | 9.27 | 20.70 | 19.37 | 13.50 | 11.34 |
| 11.20 | 9.81 | 5.70 | 6.22 | 6.50 | 7.45 |
| 12.70 | 11.20 | 19.60 | 18.31 | 19.70 | 19.99 |
| 5.20 | 4.46 | 16.00 | 12.25 | 6.00 | 6.45 |
| 11.80 | 11.18 | 2.50 | 2.05 | 14.60 | 15.44 |

*measured by ASTM D 287-92

EXAMPLE 2

The procedure of Example 1 was repeated for predicting pour point for crude oil fractions. Table 7 illustrates the quality of the predicted pour point for each sample in the training set. The data represent the value for pour point for the 428°–455° F. boiling range.

TABLE 7

PREDICTED VS. MEASURED POUR (°F.)

| MEASURED* | PREDICTED |
|---|---|
| −44 | −55 |
| −49 | −59 |
| −41 | −39 |
| −33 | −30 |
| −31 | −32 |
| −37 | −30 |
| −32 | −36 |
| −63 | −76 |
| −112 | −121 |
| −39 | −41 |
| −32 | −48 |
| −62 | −53 |
| −38 | −49 |
| −72 | −62 |
| −162 | −168 |
| −47 | −54 |
| −82 | −84 |
| −70 | −86 |

TABLE 7-continued

PREDICTED VS. MEASURED POUR (°F.)

| MEASURED* | PREDICTED |
|---|---|
| −64 | −60 |
| −35 | −40 |
| −85 | −62 |
| −39 | −36 |
| −55 | −60 |
| −56 | −58 |
| −46 | −33 |
| −41 | −41 |
| −134 | −140 |
| −34 | −32 |
| −134 | −124 |
| −39 | −44 |
| −32 | −35 |
| −57 | −49 |
| −158 | −125 |
| −35 | −35 |
| −29 | −28 |
| −94 | −90 |
| −36 | −33 |
| −48 | −38 |
| −34 | −39 |
| −34 | −36 |
| −48 | −62 |
| −46 | −33 |
| −42 | −48 |
| −43 | −37 |
| −53 | −61 |
| −20 | −20 |

*measured by ASTM D 97-87

EXAMPLE 3

Figure 2:
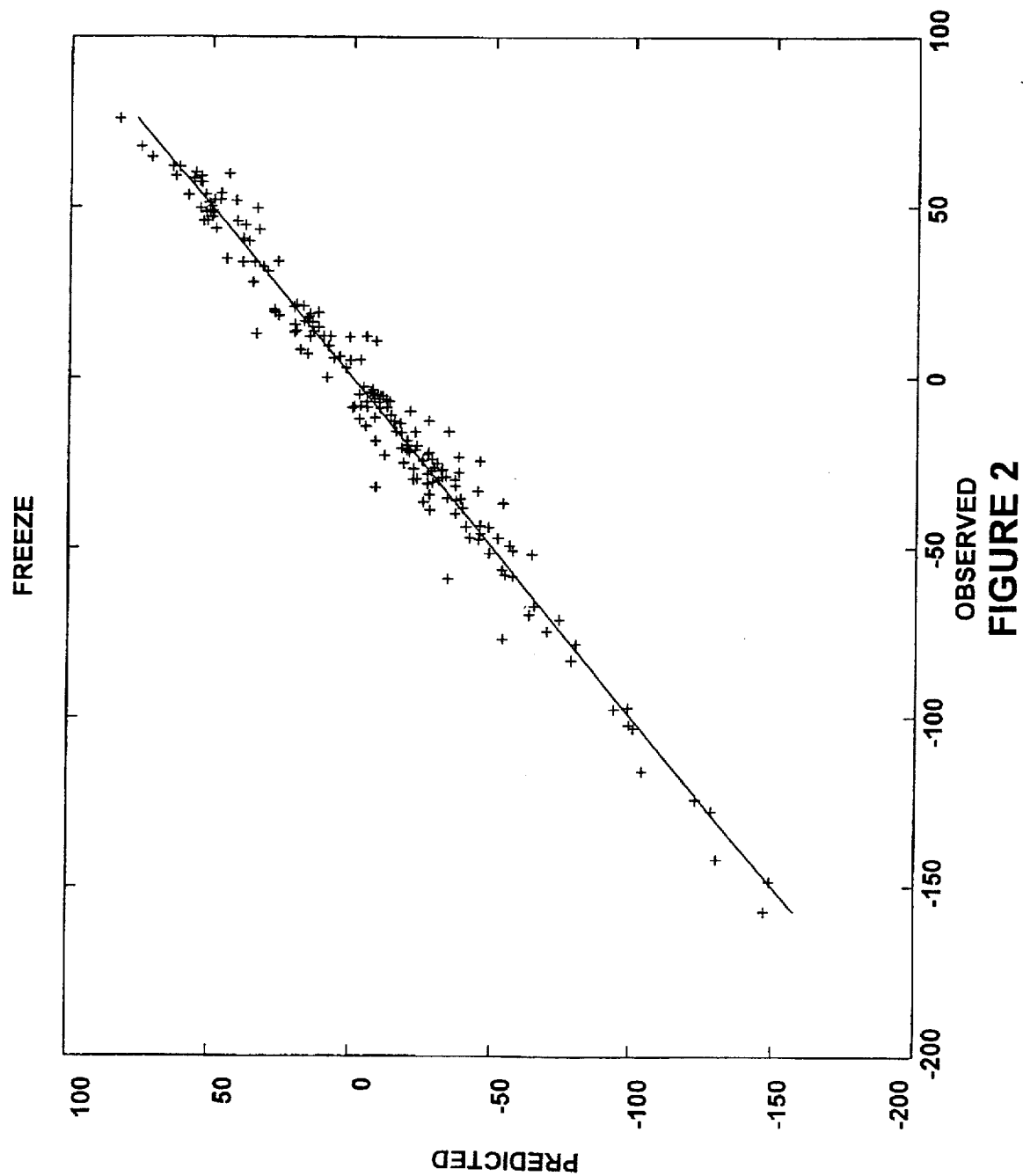
FIG. 2 is a plot of predicted vs. observed values of freeze points for crude oils.
Figure 3:
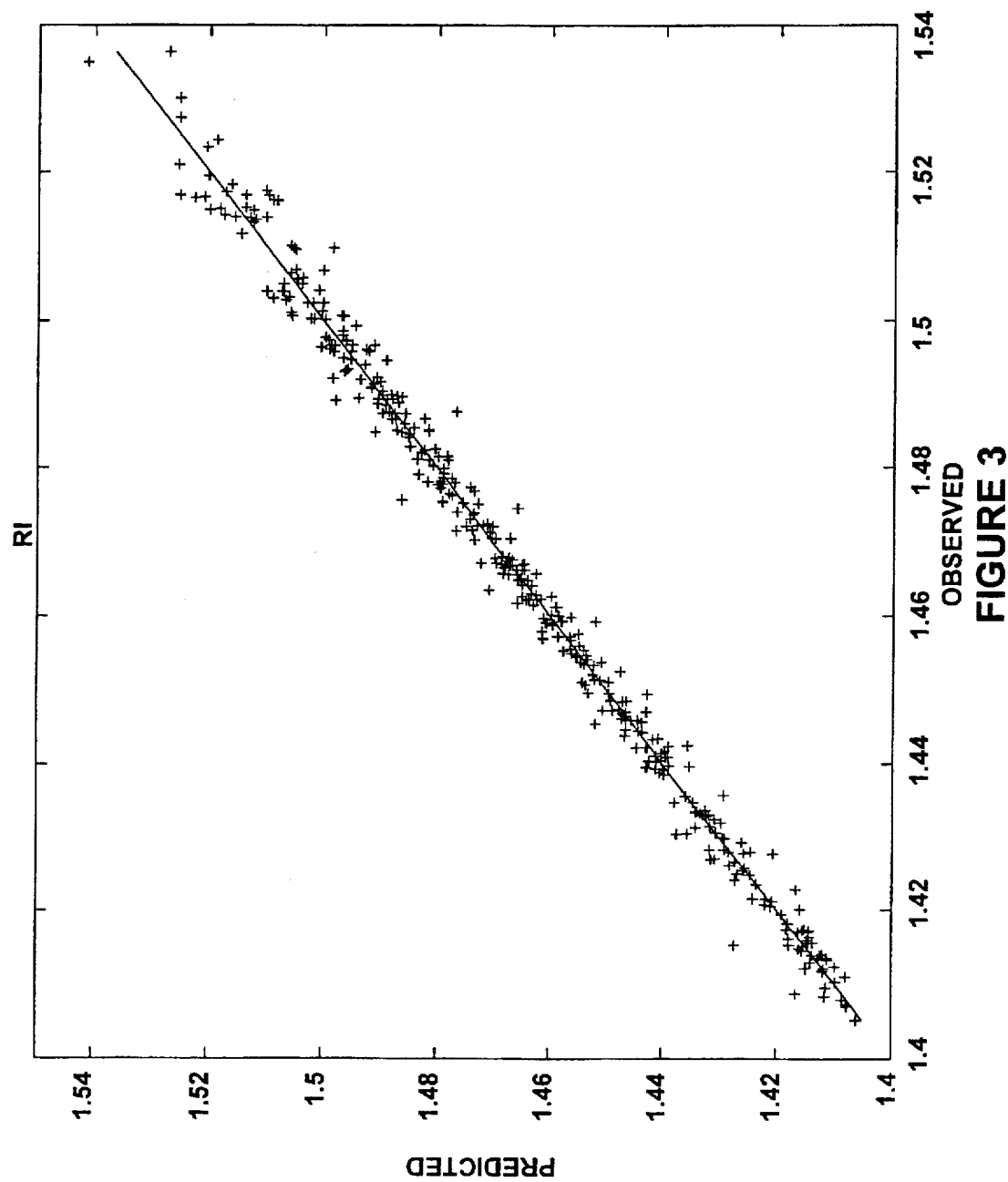
FIG. 3 is a plot of predicted vs. observed values of refractive indices for crude oils.
Figure 4:
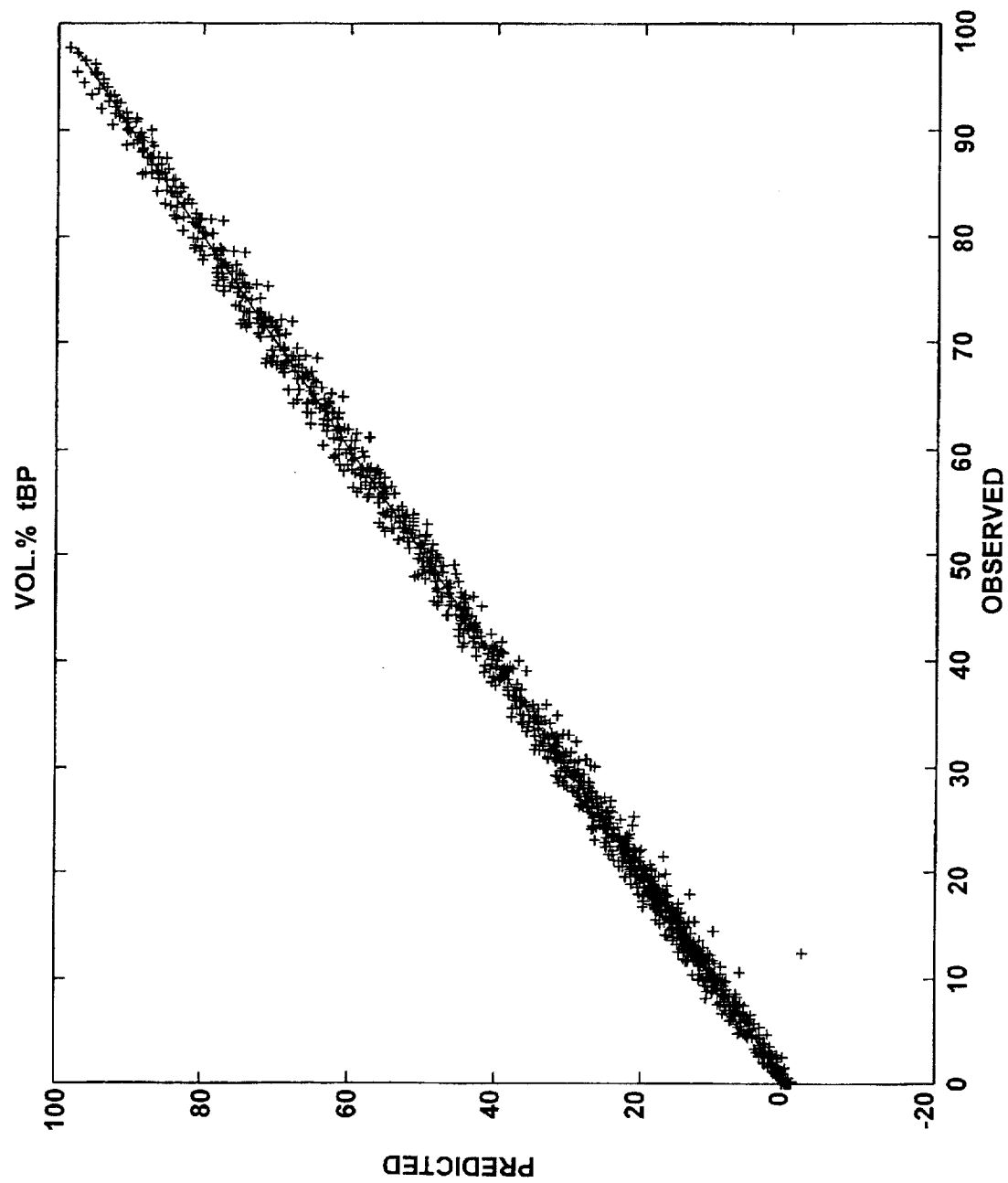
FIG. 4 is a plot of predicted vs. observed values of volume percent true boiling point for crude oils.

The procedure of Example 1 was repeated for predicting cloud points, freeze points, refractive indices and vol % true boiling point yield for the crude oils of Example 1. FIG. 1 is a plot of predicted vs. observed cloud point. FIG. 2 is a plot of predicted vs. observed freeze points. FIG. 3 is a plot of predicted vs. observed refractive indices. FIG. 4 is a plot of predicted vs. observed cumulative volume percent true boiling point yields.

EXAMPLE 4

Figure 5:
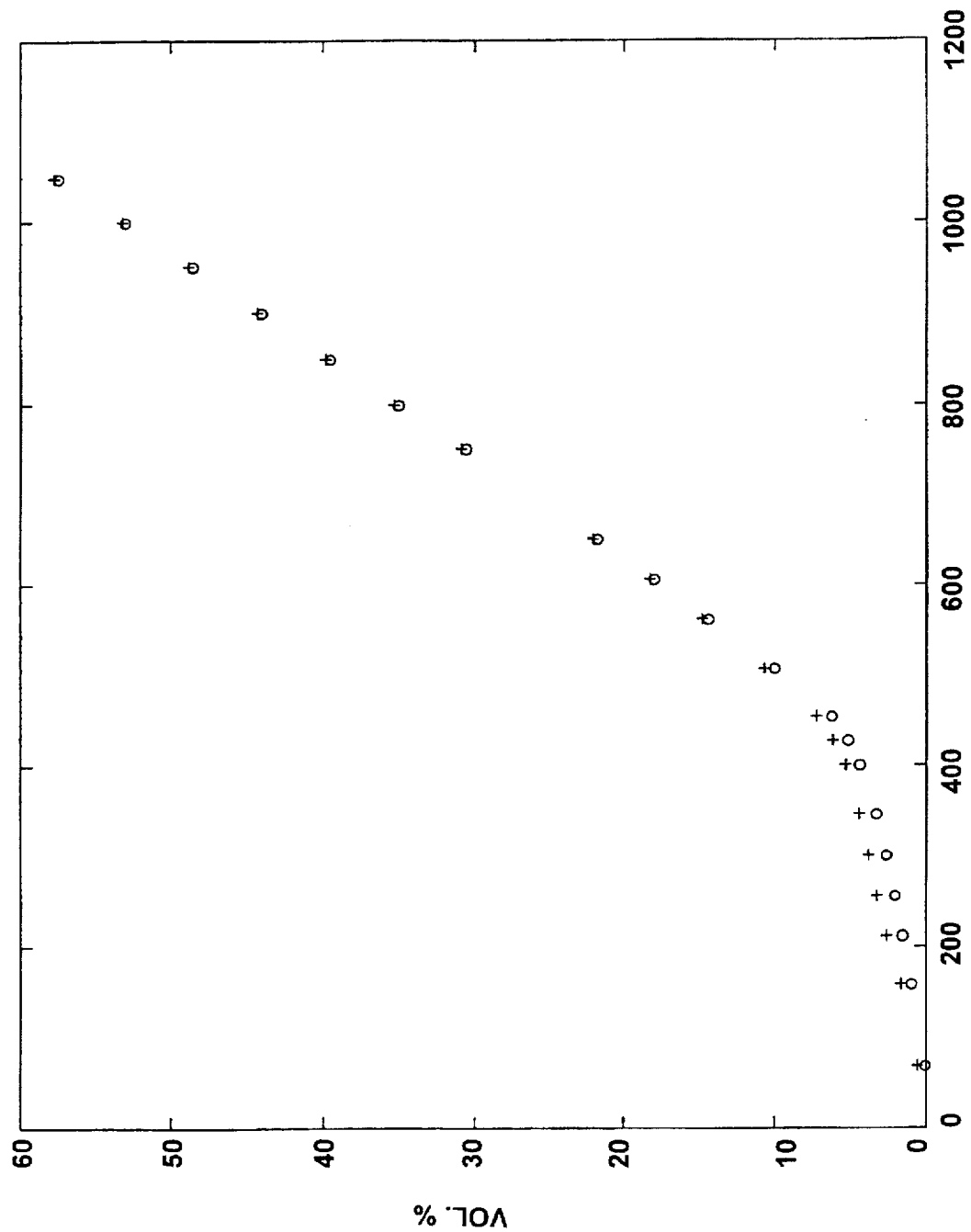
FIGS. 5, 6 and 7 are plots of predicted and observed values of vol % vs. true boiling point for individual crude oils.
Figure 6:
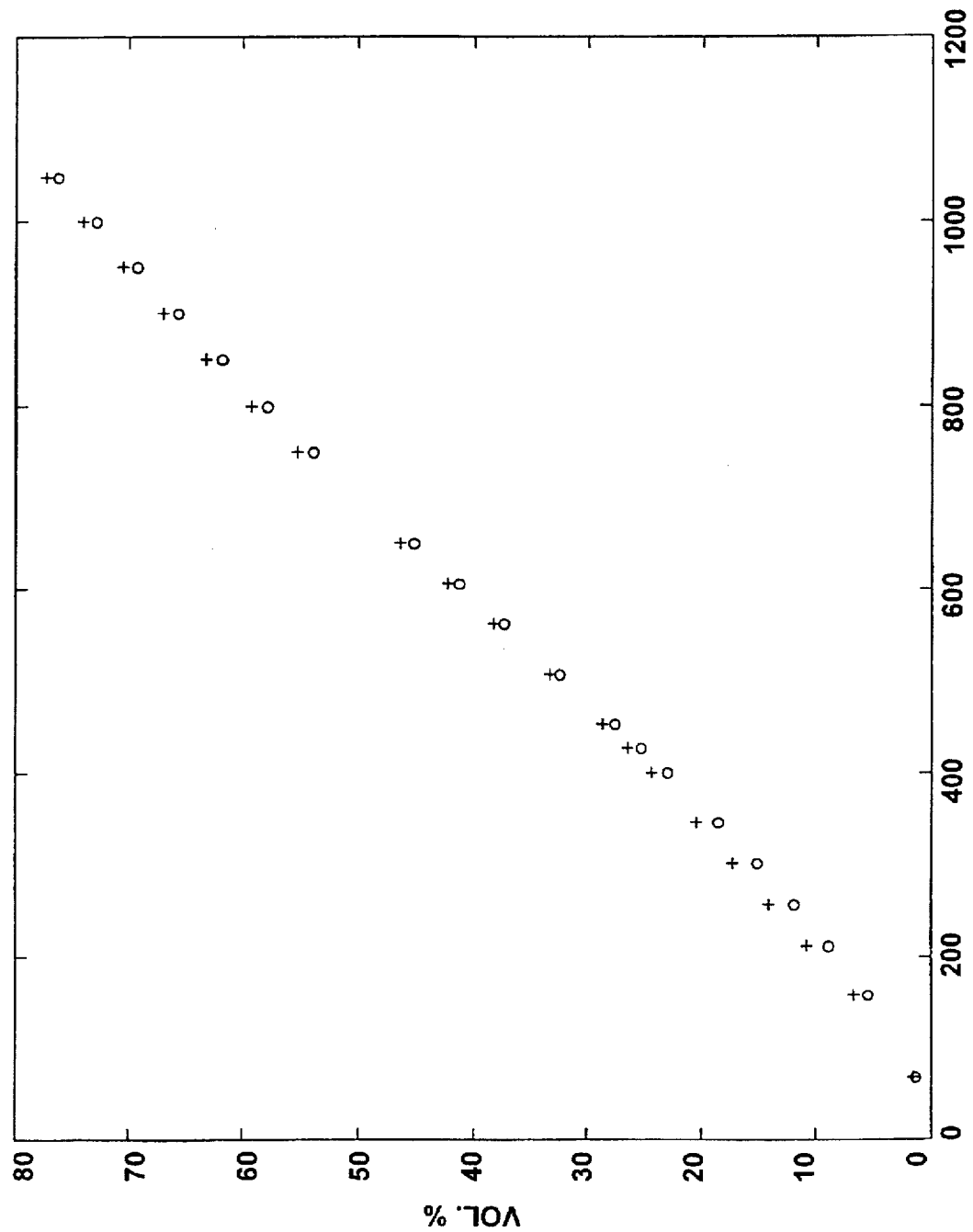
Figure 7:
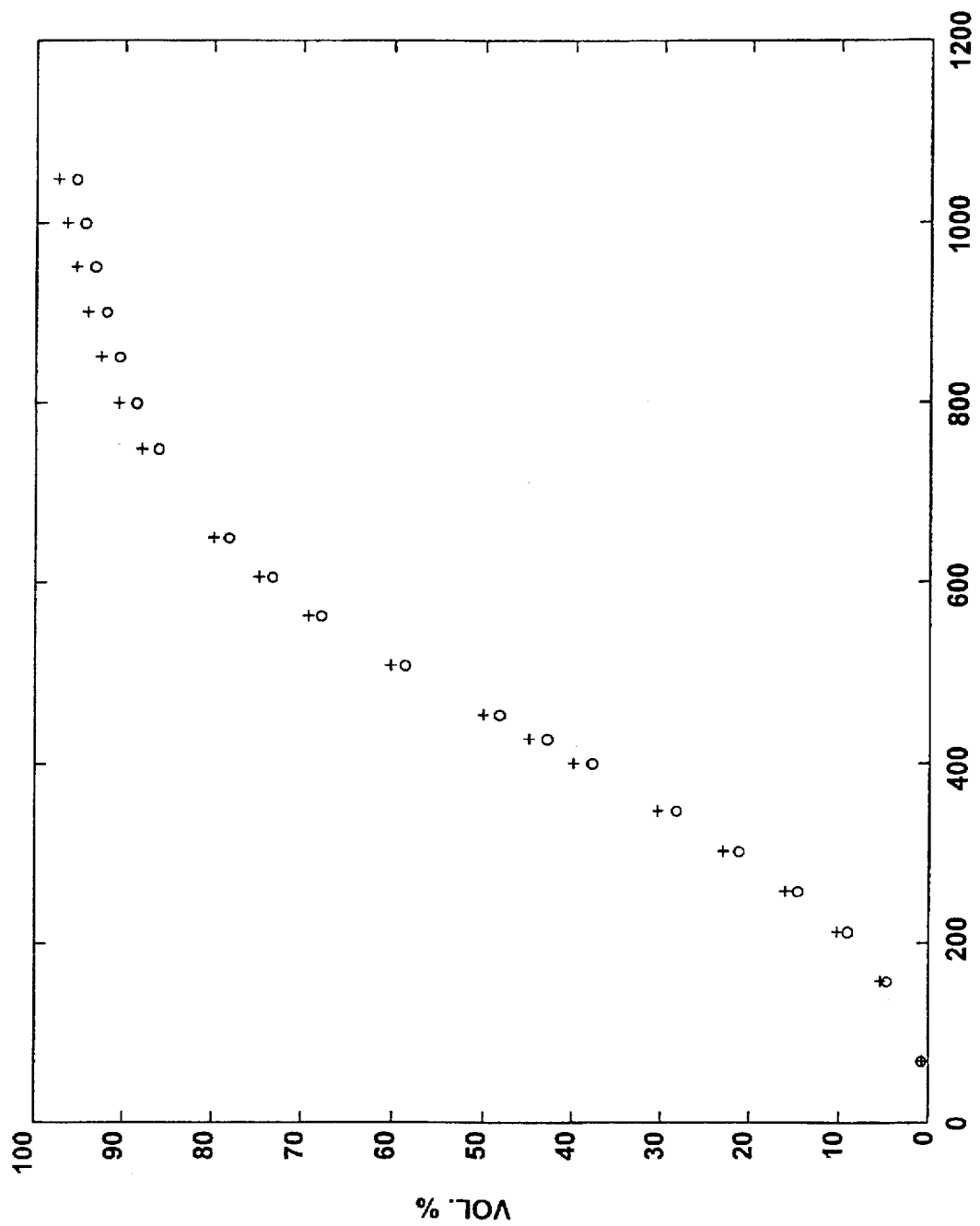
Figure 8:
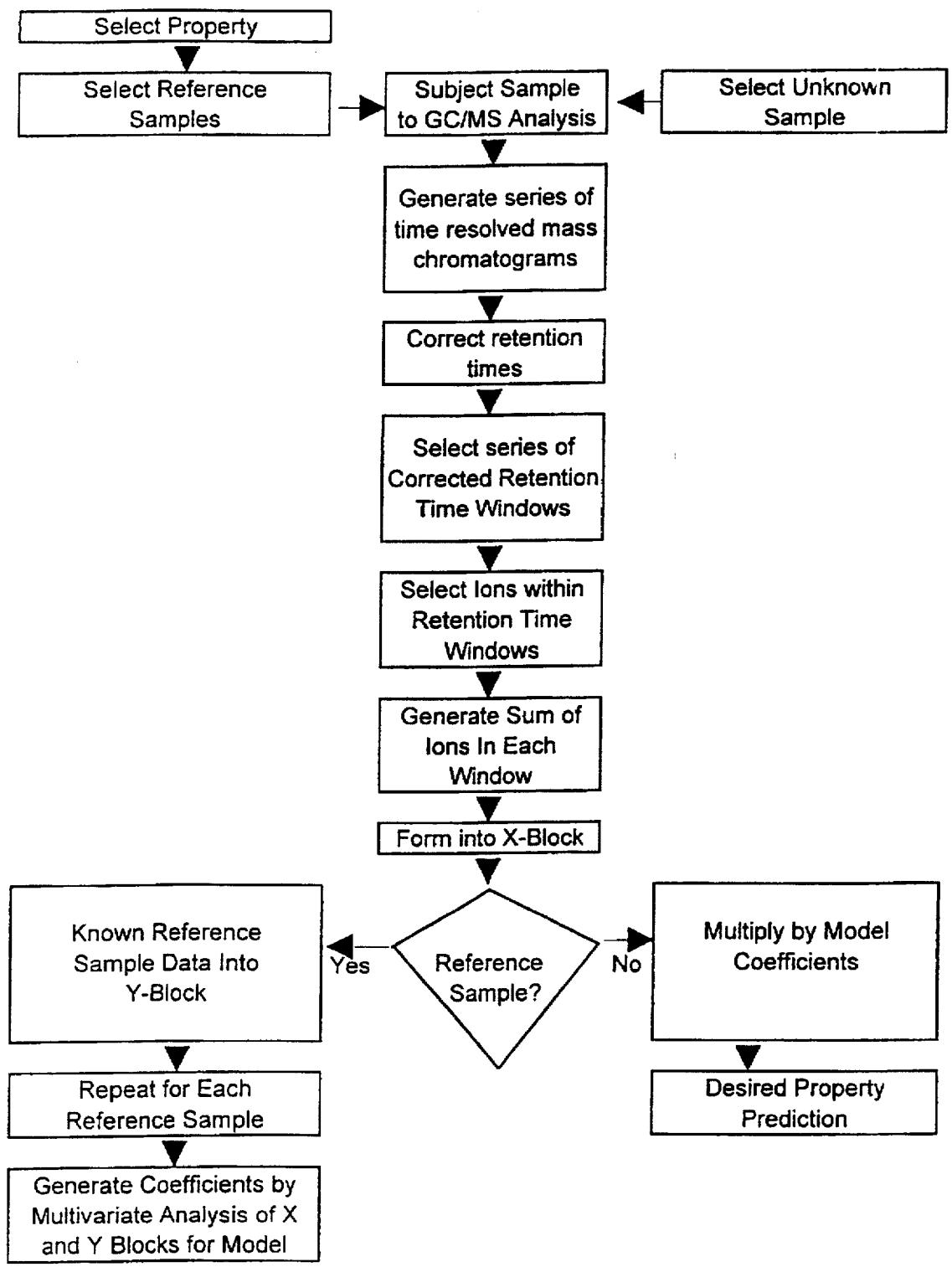
FIG. 8 is a schematic flow diagram for predicting properties of crude oils.

The plot of FIG. 4 contains numerous observations of predicted vs. observed vol % true boiling yields. This example shows the comparison between the predicted vs. observed cumulative vol % true boiling point yields for three of the individual crudes contributing to FIG. 4. The results for these three individual crudes are shown in FIGS. 5–7. In these figures, "+" is predicted and "o" is observed.

What is claimed is:

1. A method for predicting the chemical, performance, perceptual or physical properties of a crude oil which comprises:
   (a) selecting at least one property of the crude oil or its boiling fractions;
   (b) selecting reference samples, said reference samples containing characteristic chemical compound types present in the crude oil or its boiling fractions and which have known values of the properties selected in step (a);
   (c) producing a training set by the steps of:
      (1) injecting each reference sample into a gas chromatograph which is interfaced to a mass spectrometer thereby causing at least a partial separation of the hydrocarbon mixture into constituent chemical components and recording retention times of the at least partially separated components;
      (2) introducing the constituent chemical components of each reference sample into the mass spectrometer, under dynamic flow conditions;
      (3) obtaining for each reference sample a series of time resolved mass chromatograms;
      (4) calibrating the retention times to convert them to atmospheric equivalent boiling points;
      (5) selecting a series of atmospheric boiling point fractions;
      (6) selecting within each boiling point fraction a series of molecular and/or fragment ions, said ions being characteristic of compounds or chemical compound classes expected with the boiling point fraction;
      (7) (i) recording the total amount of mass spectral ion intensity of each characteristic compound or compound group selected in step c(6); and optionally (ii) multiplying total amounts of mass spectral ion intensities of each characteristic compound or chemical compound group from 7(i) by weighting factors to produce either weight or volume percent data;
      (8) forming the data from steps c(6) and either of c(7)(i) or c(7)(ii) into a X-block matrix;
      (9) forming the property data selected in (a) for reference samples selected in (b) into a Y-block matrix;
      (10) analyzing the data from steps c(8) and c(9) by multivariate correlation techniques including Partial Least Squares, Principal Component Regression, or Ridge Regression to produce a series of coefficients;
   (d) subjecting a crude oil or its boiling fractions to steps c(1) to c(3) in the same manner as the reference samples to produce a series of time resolved mass chromatograms;
   (e) repeating steps c(4) to c(8) for each mass chromatogram from step (d);
   (f) multiplying the matrix from step (e) by the coefficients from step c(10) to produce a predicted value of the property or properties for the crude oil or its boiling fractions.

2. The method of claim 1 wherein the gas chromatograph is a capillary gas chromatograph and the mass spectrometer is a quadrupole mass spectrometer.

3. The method of claim 1 wherein the gas chromatograph and mass spectrometer are operated under repeatable conditions.

4. The method of claim 1 wherein the selection of a series of molecular and/or fragment ions characteristic of compounds or compound classes is accomplished using Chemist's Rules.

5. The method of claim 1 wherein the selection of a series of molecular and/or fragment ions characteristic of compounds or compound classes is accomplished using Hydrocarbon Type Analysis.

6. The method of claim 1 wherein data from the gas chromatograph and mass spectrometer are stored in a computer.

7. The method of claim 1 wherein data from steps (c) to (f) are treated in a computer.

8. The method of claim 1 wherein other chemical or physical properties of the hydrocarbon mixture are selected.

9. The method of claim 1 wherein the data are collinear.

10. The method of claim 1 wherein the selected series of retention time windows are analyzed by a combination of Hydrocarbon Type Analysis and Chemist's Rules.

11. The method of claim 1 wherein the multivariate correlation technique is Partial Least Squares.

* * * * *

UNITED STATES PATENT AND TRADEMARK OFFICE
CERTIFICATE OF CORRECTION

PATENT NO.   : 5,699,269
DATED        : December 16, 1997
INVENTOR(S)  : Terrence R. Ashe, Stilianos G. Roussis, James W. Fedora, Gerald Felsky, William P. Fitzgerald It is certified that error appears in the above-indentified patent and that said Letters Patent is hereby corrected as shown below:

Column 5, line 13, after "masses for" insert --compounds of interest. For example, paraffinic hydrocarbons yield fragment ions at masses 43, 57, 71, 85, . . . daltons, and these masses may be used as diagnostic of this class of compounds. Moreover, when coupled with retention time data, it is possible to identify concentrations of specific compounds within this class of compounds. In a similar manner, training sets for other chemical, perceptual, performance or physical properties may be developed by correlating compositional data with other properties of interest, e.g., boiling range, viscosity, API gravity and the like. The result of a mathematical treatment such as PLS/PCR/RR of the training set is a set of coefficients for the properties of interest.--

Signed and Sealed this

Eighteenth Day of August, 1998

*Attest:*

BRUCE LEHMAN

*Attesting Officer*     *Commissioner of Patents and Trademarks*